United States Patent
Braun et al.

(10) Patent No.: US 7,479,521 B2
(45) Date of Patent: Jan. 20, 2009

(54) TRIS(HYDROXYMETHYL) ACRYLAMIDOMETHANE POLYMER, INVERSE LATEX AND MICROLATEX CONTAINING SAME, USE OF SAID POLYMER, INVERSE LATEX AND MICROLATEX

(75) Inventors: Olivier Braun, Naves (FR); Paul Mallo, Croissy sur Seine (FR); Bernard Pucci, Molleges (FR); Guy Tabacchi, Paris (FR)

(73) Assignee: Societe d'Exploitation de Produits pour les Industries Chimiques (SEPPIC), Paris (FR)

( * ) Notice: Subject to any disclaimer, the term of this patent is extended or adjusted under 35 U.S.C. 154(b) by 229 days.

(21) Appl. No.: 10/493,154

(22) PCT Filed: Oct. 4, 2002

(86) PCT No.: PCT/FR02/03394

§ 371 (c)(1),
(2), (4) Date: Sep. 7, 2004

(87) PCT Pub. No.: WO03/033553

PCT Pub. Date: Apr. 24, 2003

(65) Prior Publication Data

US 2005/0014893 A1    Jan. 20, 2005

(30) Foreign Application Priority Data

Oct. 17, 2001  (FR) .................................. 01 1361

(51) Int. Cl.
C08L 33/26   (2006.01)
C08F 222/38  (2006.01)

(52) U.S. Cl. ................. 524/555; 524/565; 524/801
(58) Field of Classification Search ................. 524/555, 524/565, 801
See application file for complete search history.

(56) References Cited

U.S. PATENT DOCUMENTS 3,591,387 A * 7/1971 Brust et al. ............... 430/627
3,733,196 A * 5/1973 Abel et al. ................ 430/543

FOREIGN PATENT DOCUMENTS

| EP | 0 040 124 A | 11/1981 |
| FR | 2 785 801 A | 5/2000 |
| WO | WO 88 09981 A | 12/1998 |
| WO | WO 00 01757 | 1/2000 |

* cited by examiner

*Primary Examiner*—Kelechi C Egwim
(74) *Attorney, Agent, or Firm*—Young & Thompson

(57) ABSTRACT

The invention concerns a linear or crosslinked polymer, characterized in that it is obtainable either by copolymerizing N-[2-hydroxy-1,1-bis(hydroxymethyl)-ethyl]-propenamide, or by copolymerizing N-[2-hydroxy-1,1-bis(hydroxymethyl) ethyl][-propenamide with one or several monomers selected among cationic monomers, monomers comprising at least a strong acid function, partly salified or completely salified, monomers comprising at least a weak acid function, partly salified or completely salified or neutral monomers. The invention also concerns inverse latex or microlatex containing such a polymer. The invention further concerns the uses of said polymer in cosmetic or pharmaceutical compositions, as thickening agents in industrial or household detergents, as additives for assisted recovery of oil, as rheology modifier for drilling fluid or as flocculants for water treatment.

4 Claims, No Drawings

TRIS(HYDROXYMETHYL) ACRYLAMIDOMETHANE POLYMER, INVERSE LATEX AND MICROLATEX CONTAINING SAME, USE OF SAID POLYMER, INVERSE LATEX AND MICROLATEX

BACKGROUND OF THE INVENTION

1. Field of the Invention

The present patent application relates to novel polymers, to water-in-oil inverse latexes and water-in-oil inverse microlatexes comprising them, to their process of preparation and to their use as flocculating, superabsorbing or rheology-modifying thickening agent.

2. Related Art

During studies into the development of novel flocculating or superabsorbing thickening agents having a prolonged stability over time, the Applicant Company became interested in polymers of N-[2-hydroxy-1,1-bis-(hydroxymethyl)ethyl] propenamide, also known as tris-(hydroxymethyl)acrylamidomethane or THAM:

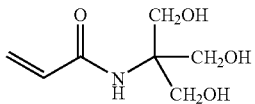

THAM is disclosed in the European patent application published under the number EP 0 900 786.

SUMMARY OF THE INVENTION

The subject invention is a method and composition comprising an oil phase, an aqueous phase, at least one emulsifying agent of water-in-oil (W/O) type and at least one emulsifying agent of oil-in-water (O/W) type, in the form either of a self-invertible inverse latex comprising from 20% to 70% by weight, and preferably from 25% to 40% by weight, of a linear or crosslinked polymer, characterized in that it is capable of being obtained either by homopolymerization of N-[2-hydroxy-1,1-bis(hydroxymethyl)ethyl] propenamide or by copolymerization of N-[2-hydroxy-1,1-bis(hydroxymethyl)ethyl] propenamide with one or more monomers chosen from cationic monomers, monomers comprising at least one, partially salified or completely salified, strong acid functional group, monomers comprising at least one, partially salified or completely salified, weak acid functional group, or neutral monomers, or of a self-invertible inverse microlatex comprising from 10% to 50% by weight, and preferably from 10% to 30% by weight, of said polymer.

DESCRIPTION OF PREFERRED EMBODIMENTS

According to a first aspect of the present invention, a subject matter of the latter is a linear or crosslinked polymer, characterized in that it is capable of being obtained either by homopolymerization of N-[2-hydroxy-1,1-bis(hydroxymethyl)ethyl]propenamide or by copolymerization of N-[2-hydroxy-1,1-bis(hydroxy-methyl)ethyl]propenamide with one or more monomers chosen from cationic monomers, monomers comprising at least one, partially salified or completely salified, strong acid functional group, monomers comprising at least one, partially salified or completely salified, weak acid functional group, or neutral monomers.

The term "crosslinked polymer" denotes a nonlinear polymer which exists in the form of a three-dimensional network which is insoluble in water but which can swell in water and which thus results in the production of a chemical gel.

The term "salified" denotes, for the strong or weak acid functional groups, the alkali metal salts, such as the sodium salt or the potassium salt, or the nitrogenous base salts, such as, for example, the ammonium salt or the monoethanolamine (HO—CH$_2$—CH$_2$—NH$_3^+$) salt.

The term "copolymerization" means that the polymerization reaction employs at the two different monomers. It can in particular employ three or more than three different monomers.

When the polymerization reaction resulting in the copolymer which is a subject matter of the present invention employs one or more monomers comprising a strong acid functional group, it is generally the sulfonic acid functional group or the phosphonic acid functional group, said functional groups being partially or completely salified. Said monomer can, for example, be styrenesulfonic acid, 2-sulfoethyl methacrylate, styrenephosphonic acid, partially or completely salified, or, preferably, 2-methyl-2-[1-oxo-2-propenyl)amino]-1-propanesulfonic acid, partially or completely salified in the form of an alkali metal salt, such as, for example, the sodium salt or the potassium salt, of the ammonium salt, of a salt of an amino alcohol, such as, for example, the monoethanol-amine salt, or of an amino acid salt, such as, for example, the lysine salt.

When the polymerization reaction resulting in the copolymer which is a subject matter of the present invention employs one or more monomers comprising a weak acid functional group, it is generally the carboxylic acid functional group; said monomers are chosen more particularly from acrylic acid, methacrylic acid, itaconic acid, maleic acid, partially or completely salified, or 3-methyl-3-[(1-oxo-2-propenyl)amino]butanoic acid, partially salified or completely salified.

When the polymerization reaction resulting in the copolymer which is a subject matter of the present invention employs one or more neutral monomers, they are chosen more particularly from acrylamide, methacrylamide, vinylpyrrolidone, diacetone acrylamide, 2-hydroxyethyl acrylate, 2,3-dihydroxypropyl acrylate, 2-hydroxyethyl methacrylate, 2,3-dihydroxypropyl methacrylate or an ethoxylated derivative, with a molecular weight of between 400 and 1000, of each of these esters.

When the polymerization reaction resulting in the copolymer which is the subject matter of the present invention employs one or more cationic monomers, they are more particularly monomers comprising one or more ammonium groups or aminated precursors of these monomers; such as, for example, 2, N,N,N-tetramethyl-2-[(1-oxo-2-propenyl) amino]propanammonium chloride (AMPTAC), 2, N,N-trimethyl-2-[(1-oxo-2-propenyl)amino]propanammonium chloride, N,N,N-trimethyl-3-[(1-oxo-2-propenyl)amino] propanammonium chloride (APTAC), diallyldimethylammonium chloride (DADMAC), N,N,N-trimethyl-2-[(1-oxo-2-propenyl)]ethanammonium chloride, N,N,N-trimethyl-2-[(1-oxo-2-methyl-2-propenyl)]ethanammonium chloride, N-[2-(dimethylamino)-1,1-dimethyl]acrylamide, N-[2-(methylamino)-1,1-dimethyl]acrylamide, 2-(dimethylamino)ethyl acrylate, 2-(dimethylamino)ethyl methacrylate or N-[3-(dimethyl-amino)propyl]acrylamide.

A subject matter of the invention is more particularly the following polymers:

homopolymers of THAM, copolymers of THAM and of 2-methyl-2-[(1-oxo-2-propenyl)amino]-1-propanesulfonic acid, partially or completely salified in the sodium salt or ammonium salt form, copolymers of THAM and of acrylic acid, partially salified in the sodium salt or ammonium salt form, copolymers of THAM and of methacrylic acid, partially salified in the sodium salt or ammonium salt form, terpolymers of THAM, of acrylic acid and of acrylamide, partially salified in the sodium salt or ammonium salt form, copolymers of THAM and of 2-methyl-2-[(1-oxo-2-propenyl)amino]-1-propane-sulfonic acid, partially or completely salified in the sodium salt or ammonium salt form, copolymers of THAM and of AMPTAC, copolymers of THAM and of APTAC, copolymers of THAM and of DADMAC, copolymers of THAM and of 2-(dimethylamino)ethyl acrylate, copolymers of THAM and of 2-(dimethylamino)ethyl methacrylate, terpolymers of THAM, of AMPTAC and of acrylamide, terpolymers of THAM, of AMPTAC and of diacetone acrylamide, terpolymers of THAM, of APTAC and of acrylamide, terpolymers of THAM, of DADMAC and of diacetone acrylamide, terpolymers of THAM, of 2-(dimethylamino)ethyl acrylate and of acrylamide or terpolymers of THAM, of 2-(dimethylamino)ethyl methacrylate and of diacetone acrylamide.

According to a specific aspect of the present invention, the polymers as defined above are linear polymers.

According to another specific aspect of the present invention, the polymers as defined above are polymers crosslinked by a crosslinking agent chosen from diethylene or polyethylene compounds and very particularly from diallyloxyacetic acid or one of the salts and in particular its sodium salt, triallylamine, trimethylolpropane triacrylate, ethylene glycol dimethacrylate, diethylene glycol diacrylate, diallylurea or methylenebis(acrylamide). The crosslinking agent is generally used in the molar proportion, expressed with respect to the monomers employed, of 0.005% to 1%, in particular of 0.01% to 0.2% and more particularly of 0.01% to 0.1%.

The polymers as defined above have a molar proportion, expressed with respect to the monomers employed, of THAM monomer generally of greater than or equal to 5%, more particularly of greater than or equal to 10% and very particularly of greater than or equal to 20%.

According to a second aspect of the present invention, a subject matter of the invention is a composition comprising an oil phase, an aqueous phase, at least one emulsifying agent of water-in-oil (W/O) type and at least one emulsifying agent of oil-in-water (O/W) type, in the form of a self-invertible inverse latex comprising from 20% to 70% by weight and preferably from 25% to 40% by weight of a polymer as defined above.

The inverse latex according to the invention generally comprises from 2.5% to 15% by weight and preferably from 4% to 9% by weight of emulsifying agents, among which agents from 20% to 50%, in particular from 25% to 40%, of the total weight of the emulsifying agents present are of the water-in-oil (W/O) type and in which invention from 80% to 50%, in particular from 75% to 60%, of the total weight of the emulsifying agents are of the oil-in-water (O/W) type.

In the inverse latex as defined above, the oil phase generally represents from 15% to 50%, preferably from 20% to 25%, of its total weight. The inverse latex comprises between 5% and 60% by weight of water and more particularly between 20% and 50% by weight of water. The latex according to the invention can also comprise various additives, such as complexing agents or chain-limiting agents.

According to a third aspect of the present invention, a subject matter of the invention is a composition comprising an oil phase, an aqueous phase, at least one emulsifying agent of water-in-oil (W/O) type and at least one emulsifying agent of oil-in-water (O/W) type, in the form of a self-invertible inverse microlatex comprising from 10% to 50% by weight and preferably from 10% to 30% by weight of a polymer as defined above.

The inverse microlatex according to the invention generally comprises from 5% to 10% by weight of a mixture of surfactants of W/O type and of O/W type having an overall HLB number of greater than or equal to 9. The oil phase generally represents from 15% to 50%, preferably from 20% to 25%, of its total weight.

The term "emulsifying agent of the water-in-oil type" denotes emulsifying agents having an HLB value which is sufficiently low to provide water-in-oil emulsions, such as the surface-active polymers sold under the name of Hypermer™ or such as sorbitan esters, for example the sorbitan monooleate sold by Seppic under the name Montane™ 80, the sorbitan isostearate sold by Seppic under the name Montanem 70 or the sorbitan sesquioleate sold by Seppic under the name of Montane™ 83. When a mixture of emulsifying agents of the water-in-oil type is concerned, the HLB value to be taken into consideration is that of said mixture.

The term "emulsifying agent of the oil-in-water type" emulsifying agents having an HLB value which is sufficiently high to provide oil-in-water emulsions, such as, for example, ethoxylated sorbitan esters, such as the ethoxylated sorbitan oleate comprising 20 mol of ethylene oxide, the ethoxylated castor oil comprising 40 mol of ethylene oxide and the ethoxylated sorbitan laurate comprising 20 mol of ethylene oxide, sold by Seppic under the names Montanox™ 80, Simulsol™ OL 50 and Montanox™ 20 respectively, the ethoxylated lauryl alcohol comprising 7 mol of ethylene oxide sold by Seppic under the name Simulsolw™ P7, the ethylene decaethoxylated oleyl/cetyl alcohol sold by Seppic under the name Simulsol™ OC 710 or the polyethoxylated sorbitan hexaoleates sold by Atlas Chemical Industries under the names G-1086 and G-1096, ethoxylated nonylphenols or alkyl polyglucosides of formula (I):

$$R_1—O—(G)_x—H \quad (I)$$

such as Simulsol™ SL 8, sold by Seppic, which is an aqueous solution comprising between approximately 35% and 45% by weight of a mixture of alkyl polyglucosides consisting of between 45% by weight and 55% by weight of a compound of formula (I) in which x is equal to approximately 1.45 and $R_1$ represents a decyl radical and between 45% by weight and 55% by weight of a compound of formula (I) in which x is equal to approximately 1.45 and $R_1$ represents an octyl radical; Simulsolw™ SL10, sold by Seppic, which is an aqueous solution comprising between approximately 50% by weight and 60% by weight of a mixture of alkyl polyglucosides consisting of approximately 85% by weight of a compound of formula (I) in which x is equal to approximately 1.45 and $R_1$ represents a decyl radical, approximately 7.5% by weight of a compound of formula (I) in which x is equal to approximately 1.45 and $R_1$ represents a dodecyl radical and approximately 7.5% by weight of a compound of formula (I) in which x is equal to approximately 1.45 and $R_1$ represents a tetradecyl radical; Simulsol™ SL11, sold by Seppic, which is an aqueous solution comprising between approximately 50% by weight and 60% by weight of a mixture of alkyl polyglucosides of formula (I) in which x is equal to approximately 1.45 and $R_1$ represents an undecyl radical, or Simulsol™ SL26, sold by Seppic, which is an aqueous solution comprising between approximately 50% by weight and 60% by weight of a mixture of alkyl polyglucosides consisting of approximately 70% by weight of a compound of formula (I) in which x is equal to approximately 1.45 and $R_1$ represents a dodecyl radical, approximately 25% by weight of a compound of formula (I) in which x is equal to approximately 1.45 and $R_1$ represents a tetradecyl radical and approximately 5% by weight of a compound of formula (I) in which x is equal to approximately 1.45 and $R_1$ represents a hexadecyl radical.

The oil phase of the inverse latex or of the inverse microlatex described above is composed either:

of a commercial mineral oil comprising saturated hydrocarbons of paraffin, isoparaffin or cycloparaffin type exhibiting, at ambient temperature, a density between 0.7 and 0.9 and a boiling point of greater than 180° C., such as, for example, Isopar™ M, Isopar™ L, Isopar™E or Isopar™G, Exxol™ D 100 S, sold by Exxon, or white mineral oils in accordance with the FDA 21 CFR 172.878 and FR 178.3620 (a) regulations, such as Marcol™ 52 or Marcol™82, also sold by Exxon;

or of hydrogenated polyisobutene, sold in France by Ets B. Rossow et Cie under the name Parleam-Polysynlane™ and mentioned in Michael and Irene Ash; Thesaurus of Chemical Products, Chemical Publishing Co. Inc., 1986, Volume I, page 211 (ISBN 0 7131 3603 0);

or of isohexadecane, which is identified in Chemical Abstracts by the number RN=93685-80-4 and which is a mixture of $C_{12}$, $C_{16}$ and $C_{20}$ isoparaffins comprising at least 97% of $C_{16}$ isoparaffins, among which the main constituent is 2,2,4,4,6,8,8-heptamethylnonane (RN=4390-04-9). It is sold in France by Bayer;

or of isododecane, sold in France by Bayer;

or of squalane, which is identified in Chemical Abstracts by the number RN=111-01-3 and which is a mixture of hydrocarbons comprising more than 80% by weight of 2,6,10,15,19,23-hexamethyltetracosane. It is sold in France by Sophim under the name Phytosqualane™;

or among the esters of fatty acids of formula (II):

$$R_1-(C=O)-O-[[CH_2-CH[O-[C(=O)]_m-R_2]-CH_2-O]_n-[C(=O)]_p]_q-R_3 \quad (II)$$

in which $R_1$ represents a saturated or unsaturated and linear or branched hydrocarbonaceous chain comprising from 7 to 30 carbon atoms, $R_2$ represents, independently of $R_1$, a hydrogen atom or a saturated or unsaturated and linear or branched hydrocarbonaceous chain comprising from 7 to 30 carbon atoms, $R_3$ represents, independently of $R_1$ or of $R_2$, a hydrogen atom or a saturated or unsaturated and linear or branched hydrocarbonaceous chain comprising from 1 to 30 carbon atoms, and m, n, p and q are, independently of one another, equal to 0 or to 1, it being understood that, when $R_3$ represents a hydrogen atom, q is other than 0. As compounds of formula (II), there are more particularly the compounds of formula (IIa):

$$R_1-(C=O)-O-CH_2-CH[O-[C(=O)]_m-R_2]-CH_2-O-[C(=O)]_p-R_3 \quad (IIa)$$

corresponding to the formula (II) as defined above in which q and n are equal to 1, or a mixture of compounds of formula (IIa); in this case, they are preferably either a compound of formula (IIa$_1$):

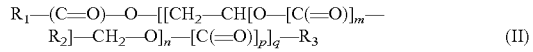

corresponding to the formula (IIa) as defined above in which m and p are equal to 0 and $R_2$ and $R_3$ represent a hydrogen atom, or a compound of formula (IIa$_2$):

$$R_1-(C=O)-O-CH_2-CH(OH)-CH_2-O-C(=O)-R_3 \quad (IIa_2)$$

corresponding to the formula (IIa) as defined above in which p is equal to 1, m is equal to 0 and $R_2$ represents a hydrogen atom, or a compound of formula (IIa$_3$):

$$R_1-(C=O)-O-CH_2-CH[O-C(=O)-R_2]-CH_2-O-C(=O)-R_3 \quad (IIa_3)$$

corresponding to the formula (IIa) as defined above in which m and p are equal to 1, or a mixture of compounds of formulae (IIa$_1$), (IIa$_2$) and/or (IIa$_3$).

As examples of compounds of formulae (IIa$_1$), (IIa$_2$) or (IIa$_3$), there are, for example, triglycerides of fatty acids or of mixtures of fatty acids, such as the mixture of triglycerides of fatty acids comprising from 6 to 10 carbon atoms sold under the name Softenol™ 3819, the mixture of triglycerides of fatty acids comprising from 8 to 10 carbon atoms sold under the name Softenol™ 3108, the mixture of triglycerides of fatty acids comprising from 8 to 18 carbon atoms sold under the name Softenol™ 3178, the mixture of triglycerides of fatty acids comprising from 12 to 18 carbon atoms sold under the name Softenol™ 3100, the mixture of triglycerides of fatty acids comprising 7 carbon atoms sold under the name Softenol™ 3107, the mixture of triglycerides of fatty acids comprising 14 carbon atoms sold under the name Softenol™ 3114 or the mixture of triglycerides of fatty acids comprising 18 carbon atoms sold under the name Softenol™ 3118, glyceryl dilaurate, glyceryl dioleate, glyceryl isostearate, glyceryl distearate, glyceryl monolaurate, glyceryl monooleate, glyceryl monoisostearate, glyceryl monostearate or a mixture of these compounds.

According to another aspect of the present invention, another subject matter of the invention is a process for the preparation of the inverse latex as defined above, characterized in that:

a) an aqueous solution comprising the monomers and the optional additives is emulsified in an oily phase in the presence of one or more emulsifying agents of water-in-oil type, b) the polymerization reaction is initiated by introduction, into the emulsion formed in a), of a free-radical initiator and optionally of a coinitiator, and then the polymerization reaction is allowed to take place, c) when the polymerization reaction is finished, one or more emulsifying agents of oil-in-water type is/are introduced at a temperature of below 50° C.

According to an alternative form of this process, the reaction medium resulting from stage b) is concentrated by distillation before the implementation of stage c).

According to a preferred implementation of the process as defined above, the polymerization reaction is initiated by a redox couple which generates hydrogensulfite ($HSO_3^-$) ions, such as the cumene hydroperoxide/sodium metabisulfite ($Na_2S_2O_5$) couple or the cumene hydroperoxide/thionyl chloride ($SOCl_2$) couple, at a temperature of less than or equal to 10° C., if desired accompanied by an agent which is a coinitiator of polymerization, such as, for example, azobis(isobutyronitrile), dilauryl peroxide or sodium persulfate, and is then carried out either quasiadiabatically, up to a temperature of greater than or equal to 50° C., or by controlling the temperature.

According to another aspect of the present invention, another subject matter of the invention is a process for the preparation of the inverse microlatex as defined above, characterized in that:

a) an aqueous solution comprising the monomers and the optional additives is emulsified in an oil phase in the presence of one or more emulsifying agents, so as to form a microemulsion, b) the polymerization reaction is initiated by introduction, into the emulsion formed in a), of a free-radical initiator and optionally of a coinitiator, and then the polymerization reaction is allowed to take place.

The polymer as defined above can be isolated from the preceding inverse latex or from the preceding inverse microlatex by the various processes known to a person skilled in the art, such as the precipitation technique, which consists in pouring the latex or the microlatex into a large excess of solvent, such as acetone, isopropanol or ethanol, or such as the spray drying technique, which is disclosed in the international publication WO 00/01757.

The polymer, the inverse polymer latex or the inverse polymer microlatex which are subject matters of the present invention can be employed, for example, as thickener for cosmetic or pharmaceutical compositions, as thickener for printing pastes for the textile industry, as thickeners for industrial or household detergents, as additives for the assisted recovery of oil, as rheology modifier for drilling muds or as flocculants for water treatment.

The following examples illustrate the present invention without, however, limiting it.

EXAMPLES

Example A (comparative)

Inverse Emulsion of a Copolymer of Sodium 2-methyl-2-[(1-oxo-2-propenyl)-amino]-1-propanesulfonate and of Acrylamide (ATBS-AA)

Procedure

The following are charged to a beaker with stirring:
80 g of deionized water,
211.6 g of a 50% by weight aqueous acrylamide solution,
93 g of a 48% by weight aqueous sodium hydroxide solution,
308.4 g of 2-methyl-2-[(1-oxo-2-propenyl)-amino]-1-propanesulfonic acid (sold in France by CIM Chemicals), and
0.47 g of a 40% by weight commercial sodium diethylenetriaminepentaacetate solution.

At the same time, an organic phase is prepared by successively introducing into a beaker, with stirring:
220 g of Isopar™ M,
27.5 g of Montane™ 80 VG (sorbitan monooleate sold by Seppic).

The aqueous phase is gradually introduced into the organic phase and is then subjected to vigorous mechanical stirring of UltraTurrax™ type, this device being sold by Ika. The emulsion obtained is then transferred to a polymerization reactor and is subjected to extensive nitrogen sparging to remove the oxygen. 5 ml of a 0.3% by weight solution of cumene hydroperoxide in Isopar™ M are then introduced.

After the time sufficient for good homogenization of the solution, 25 ml of a 0.3% by weight aqueous sodium metabisulfite solution are introduced at the rate of 0.5 ml/minute, the temperature being allowed to rise until it stabilizes. The reaction medium is maintained at this temperature for 90 minutes, the combination is then cooled to approximately 30° C. and, finally, 50 g of Simulsol™ P7 (7 EO polyethoxylated lauryl alcohol) are added in order to obtain the desired emulsion.

Evaluation of the Properties of the Latex Obtained

Viscosity at 25° C. of the latex at 1% in water (Brookfield RVT, Spindle 6, speed 5): $\eta$=11 200 mPa·s;

Viscosity at 25° C. of the latex at 1% in water+0.1% NaCl (Brookfield RVT, Spindle 6, speed 5): $\eta$=6320 mPa·s.

Example 1 (according to the invention)

Inverse Emulsion of a Copolymer of Sodium 2-methyl-2-[(1-oxo-2-propenyl)amino]-1-propanesulfonate and of N-[2-hydroxy-1,1-bis(hydroxymethyl)ethyl]propenamide (ATBS-THAM)

Procedure

The following are charged to a beaker with stirring:
356.2 g of deionized water,
221.4 g of a 55% by weight sodium 2-methyl-2-[(1-oxo-2-propenyl)amino]-1-propanesulfonate solution,
100.5 g of N-[2-hydroxy-1,1-bis(hydroxy-methyl)ethyl]propenamide, and
0.45 g of a 40% by weight commercial sodium diethylenetriaminepentaacetate solution.

At the same time, an organic phase is prepared by successively introducing into a beaker, with stirring:
218 g of Isopar™ M and
24.2 g of Montane™ 80 VG.

The aqueous phase is gradually introduced into the organic phase and is then subjected to vigorous mechanical stirring of UltraTurrax™ type. The emulsion obtained is then transferred to a polymerization reactor and is subjected to extensive nitrogen sparging to remove the oxygen. 5 ml of a 0.3% by weight solution of cumene hydroperoxide in Isopar™ M are then introduced.

After the time sufficient for good homogenization of the solution, 25 ml of a 0.3% by weight aqueous sodium metabisulfite solution are introduced at the rate of 0.5 ml/minute, the temperature being allowed to rise until it stabilizes. The reaction medium is maintained at this temperature for 90 minutes, the combination is then cooled to approximately 30° C. and, finally, 50 g of Simulsol™ P7 are added in order to obtain the desired emulsion.

Evaluation of the Properties of the Latex Obtained

Viscosity at 25° C. of the latex at 1% in water (Brookfield RVT, Spindle 6, speed 5): $\eta$=52 600 mPa·s;

Viscosity at 25° C. of the latex at 1% in water+0.1% NaCl (Brookfield RVT, Spindle 6, speed 5): $\eta$=18 000 mPa·s.

Example B (comparative)

Inverse Emulsion of a Copolymer of Sodium 2-methyl-2-[(1-oxo-2-propenyl)-amino]-1-propanesulfonate and of Acrylamide Crosslinked with MBA (ATBS-AA)

Procedure

The following are charged to a beaker with stirring:
80 g of deionized water,
211.6 g of a 50% by weight aqueous acrylamide solution,
93 g of a 48% by weight aqueous sodium hydroxide solution, 308.4 g of 2-methyl-2-[(1-oxo-2-propenyl)-amino]-1-propanesulfonic acid (sold in France by CIM Chemicals),
0.016 g of methylenebis(acrylamide) (MBA), and
0.47 g of a 40% by weight commercial sodium diethylenetriaminepentaacetate solution.

At the same time, an organic phase is prepared by successively introducing into a beaker, with stirring:
220 g of Isopar™ M,
27.5 g of Montane™ 80 VG.

The aqueous phase is gradually introduced into the organic phase and is then subjected to vigorous mechanical stirring of UltraTurrax™ type. The emulsion obtained is then transferred to a polymerization reactor and is subjected to extensive nitrogen sparging to remove the oxygen. 5 ml of a 0.3% by weight solution of cumene hydroperoxide in Isopar™ M are then introduced.

After the time sufficient for good homogenization of the solution, 25 ml of a 0.3% by weight aqueous sodium metabisulfite solution are introduced at the rate of 0.5 ml/minute, the temperature being allowed to rise until it stabilizes. The reaction medium is maintained at this temperature for 90 minutes, the combination is then cooled to approximately 30° C. and, finally, 50 g of Simulsol™ P7 are added in order to obtain the desired emulsion. Evaluation of the properties of the inverse latex obtained Viscosity at 25° C. of the latex at 1% in water (Brookfield RVT, Spindle 6, speed 5): η=40 000 mPa·s;

Viscosity at 25° C. of the latex at 1% in water+0.1% NaCl (Brookfield RVT, Spindle 6, speed 5): η=7200 mPa·s.

Example 2 (according to the invention)

Inverse Emulsion of a Copolymer of Sodium 2-methyl-2-[(1-oxo-2-propenyl)amino]-1-propanesulfonate and of N-[2-hydroxy-1,1-bis(hydroxymethyl)ethyl]propenamide Crosslinked with MBA (ATBS-THAM)

Procedure

The following are charged to a beaker with stirring:
356.2 g of deionized water,
221.4 g of a 55% by weight sodium 2-methyl-2-[(1-oxo-2-propenyl)amino]-1-propanesulfonate solution,
100.5 g of N-[2-hydroxy-1,1-bis(hydroxy-methyl)ethyl]propenamide,
0.016 g of methylenebis(acrylamide) (MBA), and
0.45 g of a 40% by weight commercial sodium diethylenetriaminepentaacetate solution.

At the same time, an organic phase is prepared by successively introducing into a beaker, with stirring:
218 g of Isopar™ M and
24.2 g of Montane™ 80 VG.

The aqueous phase is gradually introduced into the organic phase and is then subjected to vigorous mechanical stirring of UltraTurrax™ type. The emulsion obtained is then transferred to a polymerization reactor and is subjected to extensive nitrogen sparging to remove the oxygen. 5 ml of a 0.3% by weight solution of cumene hydroperoxide in Isopar™ M are then introduced.

After the time sufficient for good homogenization of the solution, 25 ml of a 0.3% by weight aqueous sodium metabisulfite solution are introduced at the rate of 0.5 ml/minute, the temperature being allowed to rise until it stabilizes. The reaction medium is maintained at this temperature for 90 minutes, the combination is then cooled to approximately 30° C. and, finally, 50 g of Simulsol™ P7 are added in order to obtain the desired emulsion.

Evaluation of the Properties of the Latex Obtained

Viscosity at 25° C. of the latex at 1% in water (Brookfield RVT, Spindle 6, speed 5): η=65 400 mPa·s;

Viscosity at 25° C. of the latex at 1% in water+0.1% NaCl (Brookfield RVT, Spindle 6, speed 5): η=14 000 mPa·s.

Example 3 (according to the invention)

Inverse Micro-Emulsion of a Copolymer of Sodium 2-methyl-2-[(1-oxo-2-propenyl)amino]-1-propanesulfonate and N-[2-hydroxy-1,1-bis(hydroxymethyl)ethyl]propenamide Crosslinked with MBA (ATBS-THAM)

Procedure

The following are charged to a beaker, with stirring:
114.8 g of deionized water,
67.2 g of a 55% by weight sodium 2-methyl-2-[(1-oxo-2-propenyl)amino]-1-propanesulfonate solution,
30.5 g of N-[2-hydroxy-1,1-bis(hydroxy-methyl)ethyl]propenamide, and
0.025 g of methylenebis(acrylamide) (MBA).

At the same time, an organic phase is prepared by successively introducing into a beaker, with stirring:
212.5 g of Isopar™ M,
30.6 g of Montane™ 83 (sorbitan sesquioleate), and
45.4 g of Montanox™ 80 (20 EO polyethoxylated sorbitan oleate).

The aqueous phase is gradually introduced into the organic phase and is then subjected to vigorous mechanical stirring of UltraTurrax™ type. The emulsion obtained is then transferred to a polymerization reactor and is subjected to extensive nitrogen sparging to remove the oxygen. 5 ml of a 0.3% by weight solution of cumene hydroperoxide in Isopar™ M are then introduced.

After the time sufficient for good homogenization of the solution, 25 ml of a 0.3% by weight aqueous sodium metabisulfite solution are introduced at the rate of 0.5 ml/minute, the temperature being allowed to rise until it stabilizes. The reaction medium is maintained at this temperature for 90 minutes and then the combination is cooled to approximately 30° C. in order to obtain the desired emulsion.

Evaluation of the Properties of the Microlatex Obtained

Viscosity at 25° C. of the latex at 1% in water (Brookfield RVT, Spindle 6, speed 5): η=65 400 mPa·s;

Viscosity at 25° C. of the latex at 1% in water+0.1% NaCl (Brookfield RVT, Spindle 6, speed 5): η=14 000 mPa·s.

Analysis of the Results

The viscosities, measured at 25° C. (Brookfield RVT, Spindle 6, speed 5; in mPa·s), are recorded in the following table; their comparison makes it possible to demonstrate that the improvement in the behavior toward salt of the inverse latexes according to the invention is inherent to the presence of THAM monomer in the polymer.

The comparison also reveals that, unexpectedly, even the uncrosslinked THAM polymers develop viscosity in aqueous solution:

| Example No. | Viscosity η of the latex at 1% in water | Viscosity η₁ of the latex at 1% in water + 0.1% NaCl |
|---|---|---|
| A | 11 200 | 6320 |
| 1 | 52 600 | 18 000 |
| B | 40 000 | 7200 |
| 2 | 65 400 | 14 000 |
| 3 | 52 600 | 18 000 |

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A composition comprising:
    a water phase component;
    an oil phase component;
    at least one emulsifying agent of water-in-oil type; and
    at least one oil-in-water emulsifying agent, wherein
        said composition is one of (i) a self-invertible inverse latex comprising from about 20% to about 70% by weight of a product polymer and (ii) a self-invertible inverse microlatex comprising from about 10% to about 50% by weight of a product polymer, and
        said product polymer is selected from the group consisting of:
            copolymers of THAM and of 2-methyl-2-[(1-oxo-2-propenyl)amino]-1-propanesulfonic acid, wherein said acid is partially or completely salified in the sodium salt or ammonium salt form,
            copolymers of THAM and of AMPTAC,
            copolymers of THAM and of APTAC,
            copolymers of THAM and of DADMAC,
            copolymers of THAM and of 2-(dimethylamino)ethyl acrylate,
            copolymers of THAM and of 2-(dimethylamino)ethyl methacrylate,
            terpolymers of THAM, of AMPTAC, and of acrylamide,
            terpolymers of THAM, of AMPTAC, and of diacetone acrylamide,
            terpolymers of THAM, of APTAC, and of acrylamide,
            terpolymers of THAM, of DADMAC, and of diacetone acrylamide,
            terpolymers of THAM, of 2-(dimethylamino)ethyl acrylate, and of acrylamide, and
            terpolymers of THAM, of 2-(dimethylamino)ethyl methacrylate, and of diacetone acrylamide.

2. The composition of claim 1, wherein the molar proportion of the THAM monomer, expressed with respect to the total amount of monomers employed, is greater than or equal to 5%.

3. The composition of claim 2, wherein the molar proportion is greater than or equal to 10%.

4. The composition of claim 3, wherein the molar proportion is greater than or equal to 20%.

* * * * *